(12) United States Patent
Watanabe et al.

(10) Patent No.: US 12,025,958 B2
(45) Date of Patent: Jul. 2, 2024

(54) CONTROL METHOD, CONTROL DEVICE, AND NON-TRANSITORY COMPUTER-READABLE RECORDING MEDIUM RECORDING PROGRAM

(71) Applicant: PANASONIC INTELLECTUAL PROPERTY MANAGEMENT CO., LTD., Osaka (JP)

(72) Inventors: Kazuhiro Watanabe, Tokyo (JP); Masaaki Harada, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 502 days.

(21) Appl. No.: 17/400,750

(22) Filed: Aug. 12, 2021

(65) Prior Publication Data

US 2021/0373504 A1 Dec. 2, 2021

Related U.S. Application Data

(63) Continuation of application No. PCT/JP2020/018227, filed on Apr. 30, 2020.

(30) Foreign Application Priority Data

Jul. 25, 2019 (JP) .................................. 2019-137112

(51) Int. Cl.
*G04G 11/00* (2006.01)
*A61M 21/00* (2006.01)
(Continued)

(52) U.S. Cl.
CPC .............. *G04G 11/00* (2013.01); *A61M 21/00* (2013.01); *G04B 25/005* (2013.01); *G04B 25/04* (2013.01);
(Continued)

(58) Field of Classification Search
CPC ....... G04B 25/005; G04B 25/04; G04G 11/00; G04G 21/025; G04G 21/04; A61M 21/00; A61M 2021/0083; A61M 2230/63
See application file for complete search history.

(56) References Cited

U.S. PATENT DOCUMENTS 9,789,878 B2 * 10/2017 Lee ........................ A61B 5/18
10,095,191 B2 * 10/2018 Heo .................... G06V 40/172
(Continued)

FOREIGN PATENT DOCUMENTS

JP 2008-086489 4/2008
JP 2011-200592 10/2011
JP 2015-207380 11/2015

OTHER PUBLICATIONS

Machine translation of JP-2011200592-A with page/line reference numbers (Year: 2011).*
(Continued)

*Primary Examiner* — Edwin A. Leon
*Assistant Examiner* — Sean R Brannon
(74) *Attorney, Agent, or Firm* — GREENBLUM & BERNSTEIN, P.L.C.

(57) ABSTRACT

A control method includes acquiring time information including a wake-up set time; acquiring a sleep state of a sleeper who is stimulated by a stimulation device; determining a change of the sleep state; causing the stimulation device to start increasing a stimulus which urges the sleeper to awake at a control start time as time before the wake-up set time by a predetermined time period; and controlling a change amount of the stimulus based on the change of the sleep state with the stimulus.

15 Claims, 15 Drawing Sheets

(51) Int. Cl.
  *G04B 25/00* (2006.01)
  *G04B 25/04* (2006.01)
  *G04G 21/02* (2010.01)
  *G04G 21/04* (2013.01)

(52) U.S. Cl.
  CPC ........... *G04G 21/025* (2013.01); *G04G 21/04* (2013.01); *A61M 2021/0083* (2013.01); *A61M 2230/63* (2013.01)

(56) References Cited

U.S. PATENT DOCUMENTS

| | | | | |
|---|---|---|---|---|
| 10,613,484 B2* | 4/2020 | Flores | ................... | G04B 19/24 |
| 2002/0080035 A1* | 6/2002 | Youdenko | ............ | G04B 23/021 |
| | | | | 340/573.1 |
| 2003/0095476 A1* | 5/2003 | Mollicone | ............. | A61M 21/00 |
| | | | | 368/73 |
| 2013/0163394 A1* | 6/2013 | Loree, IV | .............. | G04G 11/00 |
| | | | | 368/256 |
| 2013/0208576 A1* | 8/2013 | Loree, IV | .............. | G04G 11/00 |
| | | | | 368/256 |
| 2015/0305126 A1 | 10/2015 | Maeda et al. | | |
| 2015/0348390 A1 | 12/2015 | Berezhnyy et al. | | |
| 2020/0069905 A1* | 3/2020 | Tsoneva | ............... | A61B 5/4812 |
| 2021/0146089 A1* | 5/2021 | Bremer | .................. | G04C 11/00 |

OTHER PUBLICATIONS

International Search Report issued in International Pat. Appl. No. PCT/JP2020/018227, dated Jun. 16, 2020, along with an English translation thereof.

Extended European Search Report dated Mar. 15, 2022 issued in European Patent Application No. 208439023.6.

* cited by examiner

FIG. 3

| TIME | SLEEP STAGE | BODY MOVEMENT AMOUNT |
|---|---|---|
| 2019/3/27 6:28:30 | DEEP | 5 |
| 2019/3/27 6:29:40 | DEEP | 5 |
| 2019/3/27 6:30:41 | LIGHT | 105 |
| 2019/3/27 6:31:51 | LIGHT | 110 |
| 2019/3/27 6:32:50 | LIGHT | 230 |
| 2019/3/27 6:33:57 | AWAKENING | 255 |
| 2019/3/27 6:35:00 | AWAKENING | 255 |
| 2019/3/27 6:36:00 | OUT OF BEDDING | 0 |
| ... | ... | ... |

FIG. 4

| SLEEP STAGE | BODY MOVEMENT AMOUNT | ADJUSTMENT VALUE |
|---|---|---|
| LIGHT | 150 | TWO MINUTES |
| ... | ... | ... |
| ... | ... | ... |

FIG. 5

| SLEEP STAGE | BODY MOVEMENT AMOUNT | ADJUSTMENT VALUE |
|---|---|---|
| LIGHT | 110 | ONE MINUTE |
| LIGHT | 150 | TWO MINUTES |
| ... | ... | ... |
| ... | ... | ... |

FIG. 6

| SECTION | DEFINED VALUE OF CHANGE AMOUNT OF STIMULUS |
|---|---|
| T0-D1 | 0.01 |
| D1-D2 | 0.03 |
| D2-D3 | 0.07 |
| D3-D4 | 0.14 |
| D5-D6 | 0.30 |
| D6-T1 | 0.57 |
| ... | ... |

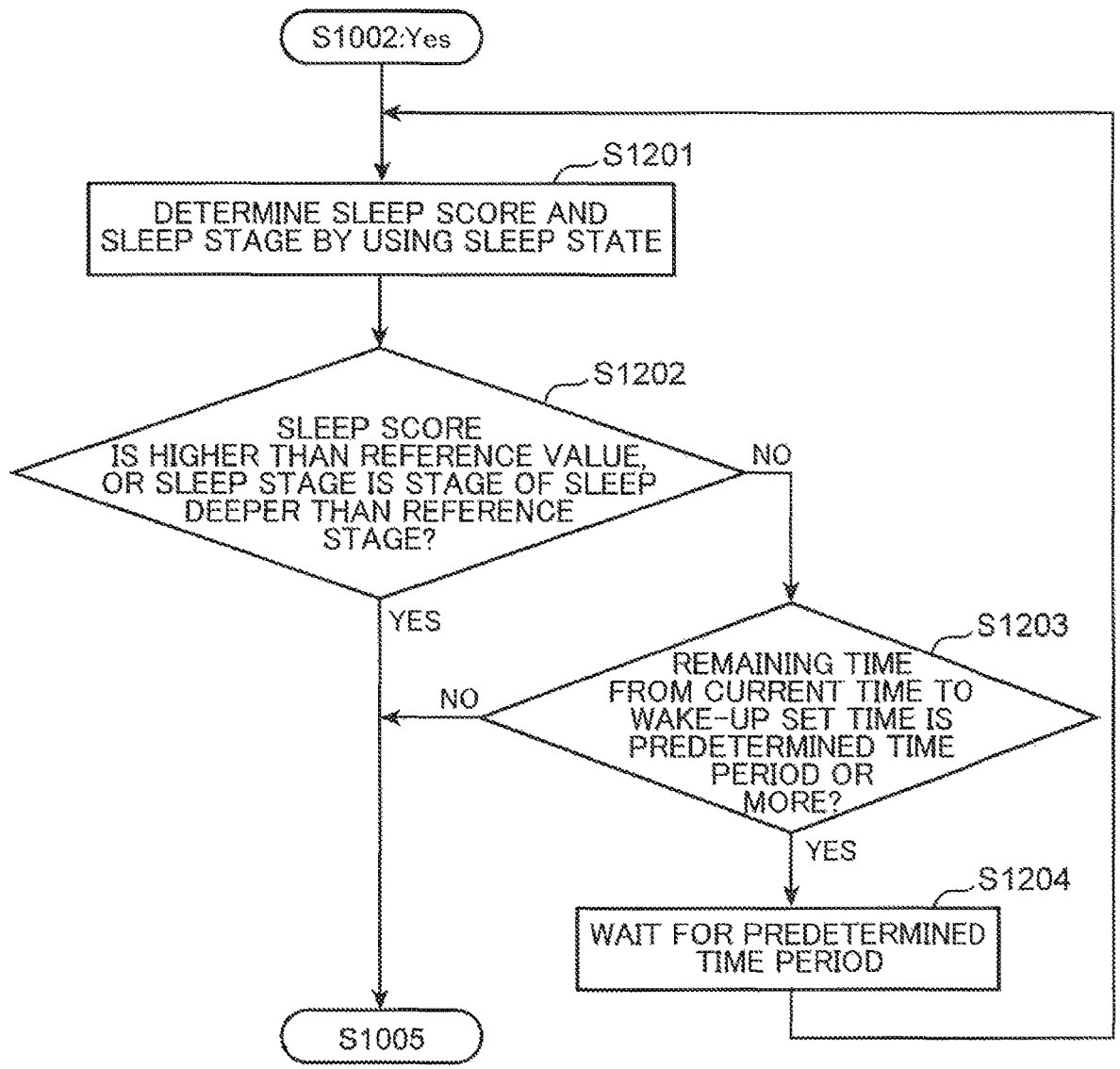

CONTROL METHOD, CONTROL DEVICE, AND NON-TRANSITORY COMPUTER-READABLE RECORDING MEDIUM RECORDING PROGRAM

TECHNICAL FIELD

The present disclosure relates to a control method, a control device, and a non-transitory computer-readable recording medium recording a program.

BACKGROUND ART

Techniques for awakening a sleeper by using an illuminating device have been studied and developed. In these days, there has been a technique for controlling illumination taking into consideration of a sleep state of a sleeper.

There has been proposed a method of urging a sleeper to awake by, for example, adjusting a light emission start time and an amount of light emission in accordance with a sleep state (see Patent Literature 1).

The method disclosed in Patent Literature 1, however, might cause an awakening level promoted by stimulation to vary among individuals. There might be a case, for example, where even when two persons in the same sleep state are illuminated with the same amount of light, the two persons have different awakening levels. This is because an individual has different sensitivity to a stimulus such as sound or light. Therefore, there may be a case where an awakening level of a person sensitive to a stimulus is increased to be so high that the person is woken up earlier than a wake-up set time. This might lead to reduction in a level of satisfaction.

CITATION LIST

Patent Literature

Patent Literature 1: Japanese Unexamined Patent Publication No. 2008-086489

SUMMARY OF INVENTION

The present disclosure provides a control method, a control device, and a non-transitory computer-readable recording medium recording a program which solve the above conventional problem.

One aspect of the present disclosure includes: acquiring time information including a wake-up set time; acquiring a sleep state of a sleeper who is stimulated by a stimulation device; determining a change of the sleep state; causing the stimulation device to start increasing a stimulus which urges the sleeper to awake at a control start time as time before the wake-up set time by a predetermined time period; and controlling a change amount of the stimulus based on the change of the sleep state with the stimulus.

According to the present disclosure, it is possible to suppress a difference in an awakening level promoted by a stimulus among individuals.

BRIEF DESCRIPTION OF DRAWINGS

FIG. 3 is a diagram showing an example of data acquired by a sensor provided in the stimulation control system according to the first embodiment of the present disclosure.

FIG. 4 is a diagram showing an example of a database of adjustment values according to the first embodiment of the present disclosure.

FIG. 5 is a diagram showing another example of a database of adjustment values according to the first embodiment of the present disclosure.

FIG. 6 is a diagram showing an example of a defined value for a change amount of a stimulus according to the first embodiment of the present disclosure.

FIG. 15 is a flow chart showing an example of a part of processing executed in a stimulation control system according to a second embodiment of the present disclosure.

DESCRIPTION OF EMBODIMENTS

Figure 1:
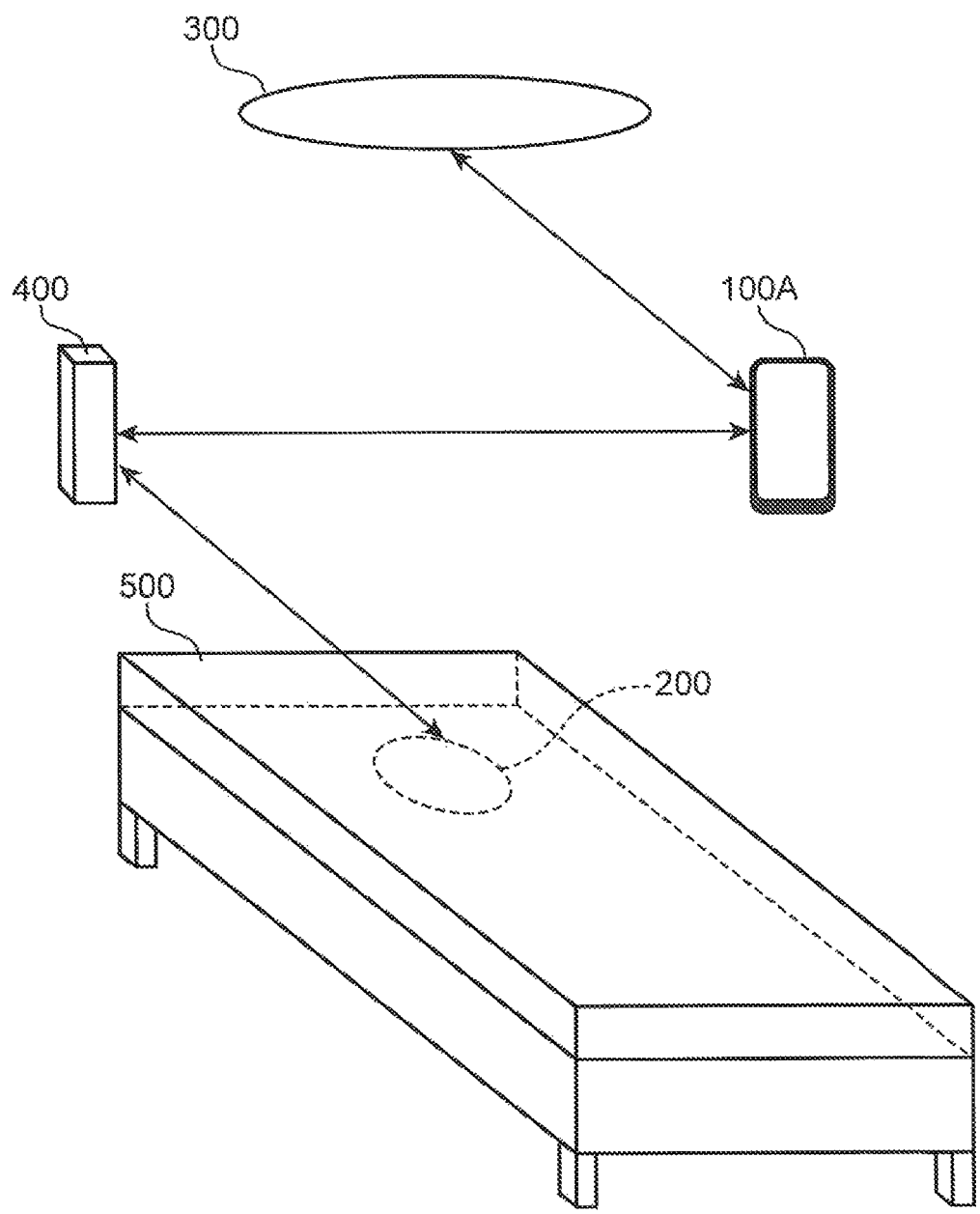
FIG. 1 is a block diagram showing a configuration example of a stimulation control system according to a first embodiment of the present disclosure.

There has been conventionally provided a method of urging a sleeper to awake by adjusting a light emission start time and an amount of light emission in accordance with a sleep state.

The conventional technique, however, might cause an awakening level promoted by stimulation to vary among individuals. For example, there may be a case where an awakening level of a person sensitive to a stimulus is increased to be so high that the person is woken up earlier than a wake-up set time. This might lead to reduction in a level of satisfaction.

By contrast, there may be a case where an awakening level of a person insensitive to a stimulus is not sufficiently increased, so that the person could not be woken up at a wake-up set time. Here, improvement in a level of satisfaction is said to be largely affected by waking comfort. In a case where awakening is abruptly urged by sound, light, or the like during a slow wave sleep period corresponding to a deep sleep state, strong sleepiness might come again. This is called sleep inertia and is known as a big factor in the reduction of a level of satisfaction. Therefore, in a state where an awakening level is not yet sufficiently increased, i.e., in a deep sleep state, urging awakening by a strong stimulus might lead to reduction in a level of satisfaction.

In order to cope with the above, one aspect of the present disclosure includes: acquiring time information including a wake-up set time; acquiring a sleep state of a sleeper who is stimulated by a stimulation device; determining a change of the sleep state; causing the stimulation device to start increasing a stimulus which urges the sleeper to awake at a control start time as time before the wake-up set time by a predetermined time period; and controlling a change amount of the stimulus based on the change of the sleep state with the stimulus.

According to this configuration, by controlling a change amount of a stimulus in accordance with a change of a sleep state with the stimulus, an excess or a deficiency of an awakening level can be suppressed even when sensitivity to the stimulus is different among individuals. Therefore, a difference in the awakening level promoted by a stimulus among individuals can be suppressed. Accordingly, it will be possible to provide comfortable waking and improve a level of satisfaction with sleep. Additionally, controlling a change amount of a stimulus enables an effect on a sleeper by a change of the stimulus to be mitigated compared to a case of direct control of a stimulus amount. For example, even in a case where a total change amount is small, when the change is abrupt, an effect of a stimulus might become strong. This is because when a stimulus amount is directly controlled in accordance with a change of a sleep state, the stimulus amount will be abruptly changed. By contrast, since in a case where a change amount of a stimulus is controlled, a stimulus amount will not be immediately changed with the control, an increase in an effect of a stimulus can be avoided.

In the above aspect, the sleep state may include a body movement amount of the sleeper, and the change amount of the stimulus is determined based on a defined value in accordance with a relationship between a change of the body movement amount with the stimulus and a defined range.

According to this configuration, a change amount of a stimulus to be applied can be altered in accordance with whether or not a change of a body movement amount is larger than an assumed change. It is therefore possible to suppress application of an excessive stimulus or a shortage of a stimulus amount.

In the above aspect, the change amount of the stimulus may be set to be smaller than the defined value in a case where the change of the body movement amount with the stimulus is larger than the defined range.

According to this configuration, a change of a stimulus can be mitigated in a case where sensitivity of a sleeper to a stimulus is higher than assumed. As a result, awakening earlier than, for example, a wake-up set time can be suppressed.

In the above aspect, the change amount of the stimulus may be set to be larger than the defined value in a case where the change of the body movement amount with the stimulus is smaller than the defined range.

According to this configuration, a change of a stimulus can be made sharp in a case where sensitivity of a sleeper to a stimulus is lower than assumed. As a result, it is possible to suppress occurrence of a situation where a sleeper cannot wake up even at a wake-up set time.

In the above aspect, the sleep state may include a sleep stage of the sleeper, and the change amount of the stimulus is determined based on the defined value in accordance with a relationship between a transition of the sleep stage in response to the stimulus and a defined transition.

According to this configuration, a change amount of a stimulus to be applied can be altered in accordance with whether or not a sleep stage after a change is a sleep stage with an assumed depth of sleep. It is therefore possible to suppress application of an excessive stimulus or a shortage of a stimulus amount.

The above aspect may further include: acquiring a change pattern of the stimulus; controlling the change amount of the stimulus based on the change pattern of the stimulus; and using a change of the sleep state with the stimulus to set a change pattern of the stimulus.

According to this configuration, since a change pattern of a stimulus as a basis for determining a change amount of the stimulus is controlled based on a change of a sleep state with the stimulus, a disparity between a change amount of a stimulus appropriate for a sleeper and a defined value is reduced. In other words, adjustment amount of a change amount of a stimulus is reduced. It is accordingly possible to decrease a calculation amount or a calculation time required for adjusting a change amount of a stimulus to a value appropriate for a sleeper.

In the above aspect, the control start time may be set using a change of the sleep state with the stimulus.

According to this configuration, since a control start time is shifted based on a change of a sleep state with a stimulus, a disparity between a change amount of a stimulus appropriate for a sleeper and a defined value is reduced. In other words, adjustment amount of a change amount of a stimulus is reduced. It is accordingly possible to decrease a calculation amount or a calculation time required for adjusting a change amount of a stimulus to a value appropriate for a sleeper.

In the above aspect, the change amount of the stimulus may be controlled at an interval of time required for estimating the sleep state.

According to this configuration, control of a change amount of a stimulus based on a change of a sleep state can be executed every time the change of the sleep state is determined. It is accordingly possible to reduce a time lag in the control behind the change of the sleep state.

In the above aspect, in a case where, as a result of controlling the change amount of the stimulus based on a change of the sleep state with the stimulus, an amount of the stimulus fails to reach a target amount at the wake-up set time, the change amount of the stimulus may be controlled so that the amount of the stimulus reaches the target amount at predetermined timing after the wake-up set time.

According to this configuration, even in a case where a stimulus amount fails to reach a target amount at a wake-up set time, an awakening level of a sleeper can be continuously increased.

In the above aspect, the predetermined timing may be time when an alarm to be given at the wake-up set time is restarted after a predetermined time period.

According to this configuration, an awakening level of a sleeper can be increased so that the sleeper can awake at timing of a subsequent alarm. Accordingly, a possibility of awakening at the timing can be increased.

In the above aspect, in a case where, as a result of controlling the change amount of the stimulus based on a change of the sleep state with the stimulus, an amount of the stimulus fails to reach a target amount at the wake-up set time, the change amount of the stimulus may be controlled so that the amount of the stimulus reaches the target amount after awakening of the sleeper.

According to this configuration, since even in a case where a stimulus amount fails to reach a target amount at a wake-up set time, the stimulus amount reaches the target amount after awakening, it is not necessary for a sleeper to operate a stimulation device after awakening.

In the above aspect, a kind of the stimulus or a mode of the stimulus may be selected in accordance with a change of the sleep state with the stimulus, and the change amount of the stimulus of the selected kind or mode may be controlled based on a change of the sleep state of the stimulus of the selected kind or mode.

According to this configuration, even when sensitivity to a kind or mode of a stimulus is different among individuals, difference in an awakening level among individuals can be suppressed.

In the above aspect, the stimulus may be at least one of light, sound, tactile vibration, wind, and heat.

According to this configuration, various stimuli can be considered a control target.

Further, these comprehensive or specific aspects may be realized by a control device, a stimulation control system, an integrated circuit, a computer program, or a non-transitory recording medium such as a computer-readable CD-ROM, or may be realized by an arbitrary combination of a control device, a stimulation control system, an integrated circuit, and a recording medium.

Embodiments to be described below each show a specific example of the present disclosure. Numerical values, shapes, configurations, elements, steps, orders of the steps shown in the embodiments below are each one example and are not intended to limit the present disclosure. Additionally, among the components in the embodiments below, components not recited in an independent claim showing a most significant concept will be described as arbitrary components. In all of the embodiments, respective contents can be combined.

1. First Embodiment

<1-1. Configuration of Stimulation Control System>

FIG. 1 is a diagram showing a stimulation control system according to a first embodiment of the present disclosure and surroundings thereof.

The stimulation control system includes a control device 100A, a sensor 200, and a stimulation device 300. The control device 100A and the stimulation device 300, and the control device 100A and a wireless router 400 communicate with each other, respectively. The sensor 200 communicates with the control device 100A via the wireless router 400. The sensor 200 is installed in a bedding 500.

For example, the control device 100A and the stimulation device 300 are connected through Bluetooth (registered trademark) communication. The control device 100A and the wireless router 400, and the sensor 200 and the wireless router 400 are connected through Wi-Fi (registered trademark) communication, respectively. A communication method for use in the connection is not limited thereto and may be common short-distance wireless communication of other method, application-specific wireless communication such as ECHONET Lite (registered trademark), cellular phone communication such as 4G (4th Generation)/LTE (Long Term Evolution), and wired communication using wires.

The control device 100A is a communication terminal. The control device 100A is, for example, a smart phone, a tablet terminal, or a smart speaker. The control device 100A receives biometric information from the sensor 200 and transmits a control instruction to the stimulation device 300, thereby controlling the stimulation device 300.

The sensor 200 senses human biometric information. The sensor 200 is installed in the bedding 500 such as a bed mattress. The sensor 200 is a sensor which acquires biometric information such as heartbeats, respiration, body movement, sweating, body temperature, or brain wave. For example, the sensor 200 may be a piezoelectric sensor, a radio sensor, an optical sensor, or an image processing sensor. Additionally, the sensor 200 may be arranged in either an upper or lower bed mattress, or incorporated in the mattress. The sensor 200 may be arranged at a leg of the bed in a case of a piezoelectric sensor, or may be arranged in the surroundings of the bedding 500 in a case of a radio or image processing sensor. The sensor 200 may be incorporated in the control device 100A or other communication terminal. Further, the sensor 200 may be directly connected with the control device 100A using wireless communication such as Bluetooth without the wireless router 400 provided therebetween.

The stimulation device 300 outputs a stimulus which urges a sleeper to awake. The stimulation device 300 is, for example, an illuminator which outputs light, a speaker which outputs sound, a vibrator which outputs tactile vibration, a blower which outputs wind, or an air-conditioner which outputs heat. A plurality of stimulation devices 300 may be provided. The stimulation device 300 may also be a device which outputs a plurality of stimuli. Further, the stimulation device 300 may be connected with the control device 100A via the wireless router 400.

In the example shown in FIG. 1, the stimulation device 300 is a ceiling light as an illuminator using light as a stimulus.

The wireless router 400 mediates communication using wireless communication. For example, the wireless router 400 may be a home gate way of HEMS (Home Energy Management System).

Figure 2:
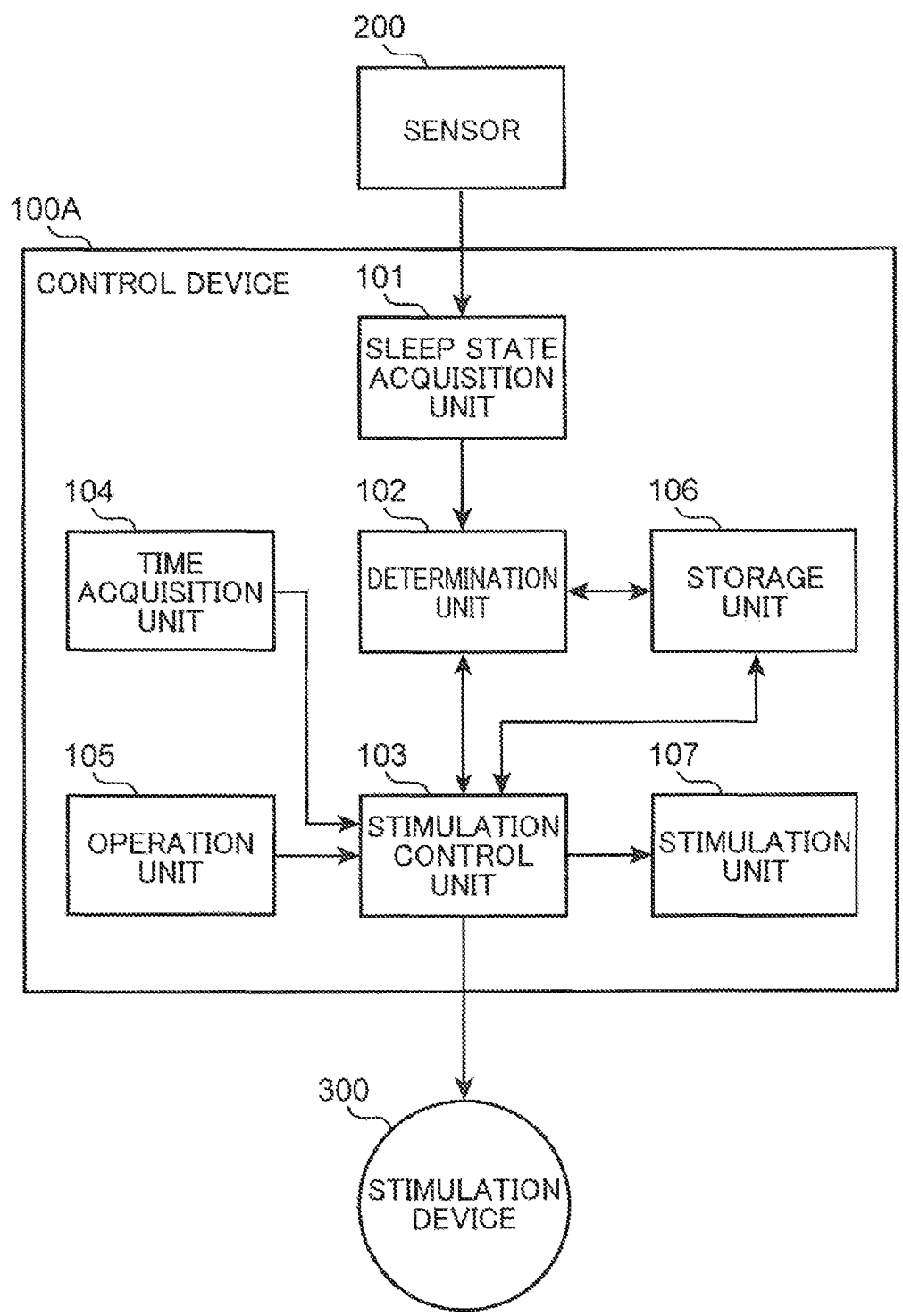
FIG. 2 is a diagram showing the stimulation control system and surroundings thereof according to the first embodiment of the present disclosure.

FIG. 2 is a diagram showing a configuration of the stimulation control system according to the first embodiment of the present disclosure.

The control device 100A includes a sleep state acquisition unit 101, a determination unit 102, a stimulation control unit 103, a time acquisition unit 104, an operation unit 105, a storage unit 106, and a stimulation unit 107.

The sleep state acquisition unit 101 acquires biometric information of a sleeper who is stimulated by the stimulation device 300. The stimulation device 300 is installed in a space where the sleeper sleeps. Specifically, the sleep state acquisition unit 101 acquires biometric information of a sleeper who sleeps in a room in which the stimulation device 300 is set from the sensor 200 installed in a mattress of a bed on which the sleeper is present. For example, biometric information includes a body movement amount and a sleep stage as shown in FIG. 3 and is acquired at a predetermined time interval. The predetermined time interval may be, for example, an interval of time required for estimating a sleep state. The acquired sleep state is stored in the storage unit 106. The sleep state acquisition unit 101 may acquire a sleep state by using biometric information to estimate a sleep state. For example, the biometric information includes data related to body movement, heartbeats, and respiration. The sleep stage can be estimated further using an elapsed time from a falling asleep time.

The determination unit 102 determines a change of asleep state. Specifically, every time a sleep state is acquired by the sleep state acquisition unit 101, the determination unit 102 determines a change of the sleep state. For example, the determination unit 102 determines a change amount of a body movement amount. The determination unit 102 also determines a transition of the sleep stage. In place of or together with a body movement amount, a change amount of the number of heartbeats or of a respiration rate may be determined.

The stimulation control unit 103 controls stimulation by the stimulation device 300. Specifically, the stimulation control unit 103 causes the stimulation device 300 to start increasing a stimulus at a control start time which is prior to a wake-up set time by a predetermined time period. More specifically, the stimulation control unit 103 sets a control start time by using a change of a sleep state with a stimulus. For example, when a control start time arrives, the stimulation control unit 103 acquires a sleep state and acquires an adjustment value associated with the acquired sleep state from such a database as shown in FIG. 4. The stimulation control unit 103 alters the control start time based on the acquired adjustment value. The stimulation control unit 103 also determines an adjustment value of the control start time based on a change of a sleep state in the control of a change amount of a stimulus immediately after start of stimulation control (in other words, in first stimulation control). For example, in a case where the change of the sleep state is larger than defined, an adjustment value is set and is added to the database so as to be associated with the sleep state before the change in a manner as shown in FIG. 5. The set adjustment value can be updated based on accumulated adjustment values. For example, the adjustment value can be updated by averaging a plurality of adjustment values associated with close sleep states. Then, when the control start time arrives, the stimulation control unit 103 causes the stimulation device 300 to start increasing a stimulus. In a case where the stimulation device 300 is in a state of outputting no stimulus, the stimulation control unit 103 will cause stimulation to start, and in a case where the stimulation device 300 is in a state of outputting a stimulus, the stimulation control unit 103 will cause an amount of a stimulus being output to be increased.

The stimulation control unit 103 also controls a change amount of a stimulus based on a change of a sleep state with a stimulus. Specifically, the stimulation control unit 103 determines a change amount of a stimulus based on a defined value in accordance with a relationship between a change of a body movement amount determined by the determination unit 102 and a defined range. The stimulation control unit 103 also determines a change amount of a stimulus based on the defined value in accordance with a relationship between a transition of a sleep stage determined by the determination unit 102 and a defined transition. The stimulation control unit 103 controls a change amount of a stimulus based on a change pattern of a stimulus. For example, as a change pattern of the stimulus, a defined value for a change amount of a stimulus is set in each section of an elapsed time from the start of stimulation as shown in FIG. 6. A change pattern of the stimulus is acquired from the storage unit 106. Thus, since a change amount is constant in each section, a change of a sleep state with a stimulus can be determined.

The stimulation control unit 103 can set a change pattern of a stimulus based on a change of a sleep state with the stimulus. For example, in a case where a change of a sleep state is larger than defined, the stimulation control unit 103 selects a pattern having a more gradual change of a stimulus. By contrast, in a case where a change of a sleep state is smaller than defined, the stimulation control unit 103 selects a pattern having a sharper change of a stimulus.

The stimulation control unit 103 also controls operation of the stimulation unit 107 based on operation accepted by the operation unit 105. Specifically, when stimulation stop operation is accepted by the operation unit 105, the stimulation control unit 103 causes the stimulation unit 107 to stop stimulation.

The time acquisition unit 104 acquires time information including a wake-up set time. Specifically, the time acquisition unit 104 acquires a wake-up set time from the storage unit 106. The time acquisition unit 104 acquires current time. The current time may be acquired through communication or acquired from a timer which is provided in the control device 100A to manage time.

The operation unit 105 accepts operation for the control device 100A. Specifically, the operation unit 105 accepts operation such as setting and stop of the stimulation unit 107.

The storage unit 106 stores information for use in the processing of the control device 100A. Specifically, the storage unit 106 stores information such as the above-described sleep state, change pattern of a stimulus, and adjustment value of a control start time.

The stimulation unit 107 outputs a stimulus which urges a sleeper to awake. Specifically, the stimulation unit 107 outputs a stimulus of a kind different from that of a stimulus output by the stimulation device 300. For example, the stimulation unit 107 is a speaker which outputs sound as an alarm.

<1-2. Processing of Stimulation Control System>

Figure 7:
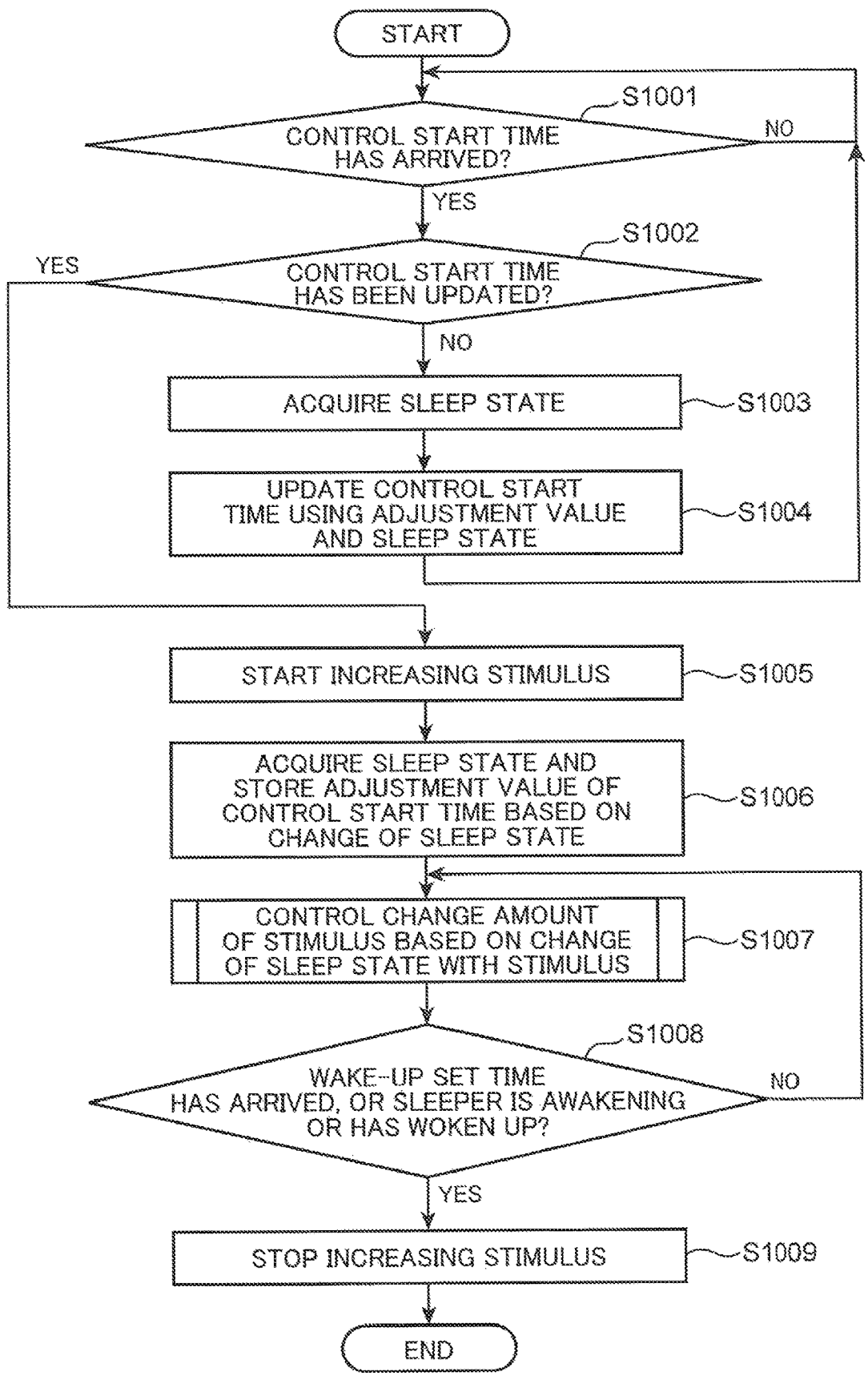
FIG. 7 is a flow chart showing an example of processing of the stimulation control system according to the first embodiment of the present disclosure.
Figure 8:
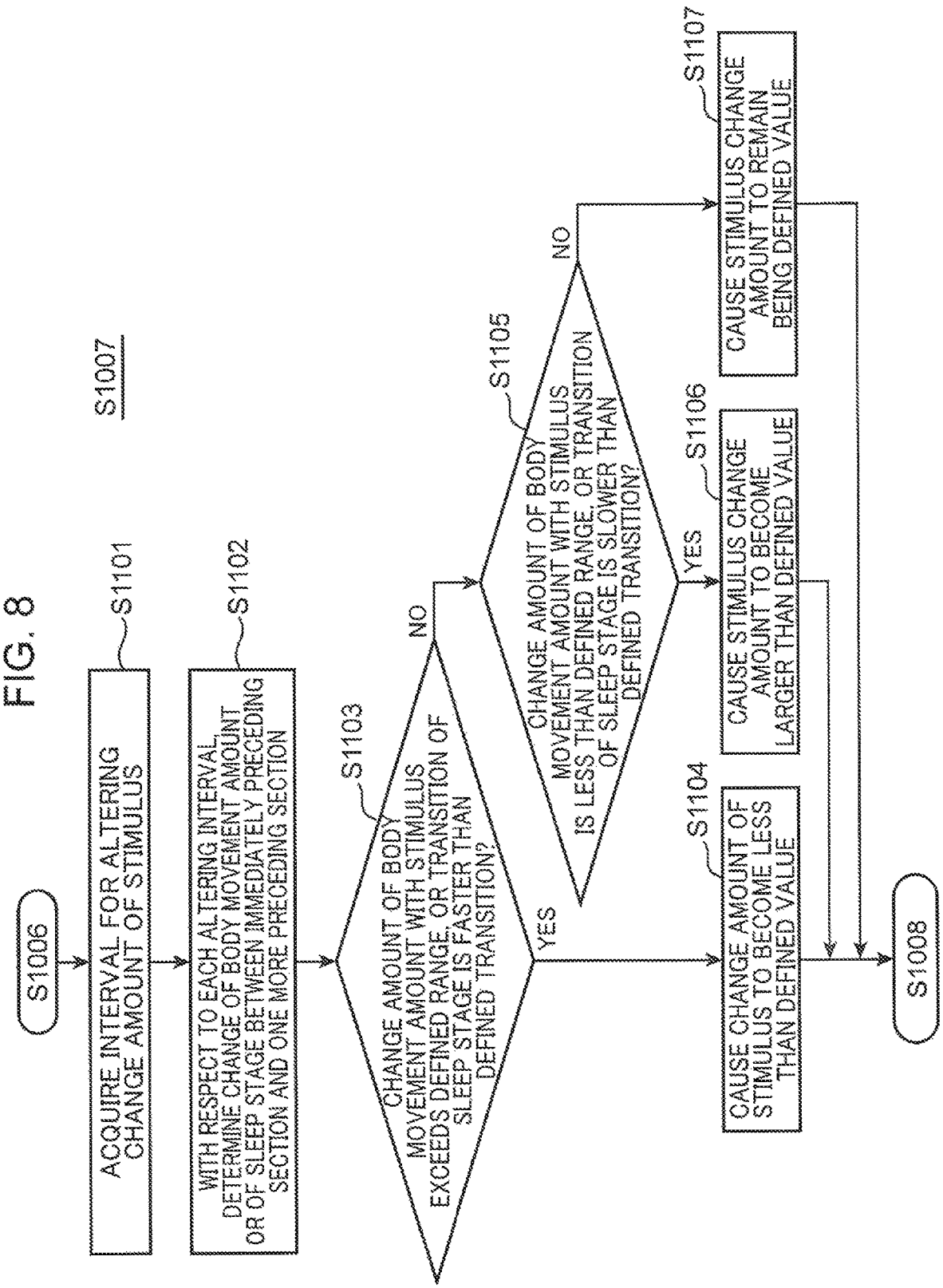
FIG. 8 is a flow chart showing an example of details of a part of processing executed in the stimulation control system according to the first embodiment of the present disclosure.
Figure 9:
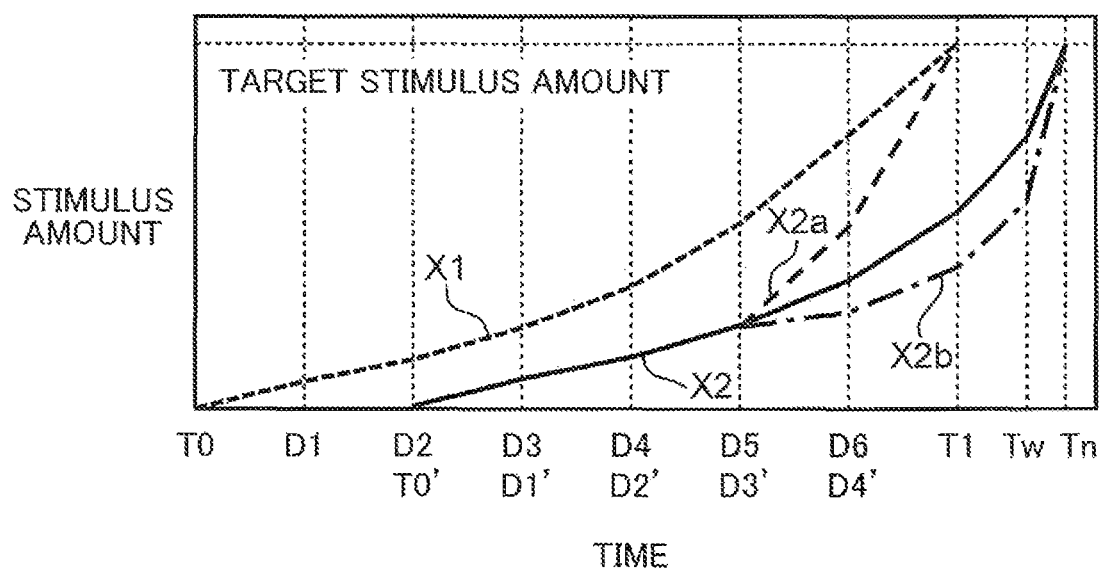
FIG. 9 is a graph showing an example of a change of a stimulus amount according to the first embodiment of the present disclosure.

Subsequently, using FIG. 7 to FIG. 9, processing of the stimulation control system will be described. FIG. 7 is a flow chart showing the processing of the stimulation control system according to the first embodiment of the present disclosure.

First, the control device 100A waits until determination is made that a control start time has arrived (Step S1001). Specifically, the stimulation control unit 103 waits for the arrival of time which is before, by a predetermined time period, a wake-up set time acquired by the time acquisition unit 104.

In a case of Yes in Step S1001, the control device 100A determines whether or not the control start time has been updated (Step S1002). Specifically, when the time before, by a predetermined time period, the wake-up set time arrives, the stimulation control unit 103 determines whether or not updating processing of the control start time has been executed. The stimulation control unit 103 also determines whether or not an adjustment value of the control start time is present in the database.

In a case of No in Step S1002, the control device 100A acquires a sleep state (Step S1003). Specifically, in a case where determination is made that the updating processing of the control start time has not been executed yet, the stimulation control unit 103 acquires, from the storage unit 106, a sleep state acquired by the sleep state acquisition unit 101.

Next, the control device 100A updates the control start time using an adjustment value and the acquired sleep state (Step S1004). Specifically, the stimulation control unit 103 refers to such a database as shown in FIG. 4 to acquire an adjustment value matching the acquired sleep state (i.e., a body movement amount and a sleep stage). The stimulation control unit 103 adds the acquired adjustment value to the control start time. Thereafter, the processing returns to Step S1001.

In a case of Yes in Step S1002, the control device 100A causes the stimulation device 300 to start increasing a stimulus (Step S1005). Specifically, the stimulation control unit 103 causes an increase of a stimulus to start because the updated control start time has arrived. Also in a case where determination is made that a matching adjustment value is not present in the database, the processing proceeds to Step S1005.

Next, the control device 100A acquires a sleep state and stores an adjustment value of the control start time based on a change of the initial sleep state (Step S1006). Specifically, when increasing a stimulus is started, the determination unit 102 determines whether or not a change of a body movement amount, of the number of heartbeats, or of a respiration rate exceeds a defined range. The determination unit 102 also determines whether or not a transition of a sleep stage is a defined transition. Details of the determination processing will be described later using FIG. 8. In a case where a change of the body movement amount or the like exceeds the defined range or in a case where the transition of the sleep stage is not the defined transition, the determination unit 102 calculates an adjustment value of the control start time based on a degree of deviation from the defined range or the defined transition. The determination unit 102 causes the calculated adjustment value to be stored in the database in the storage unit 106 so as to be associated with a sleep state before the increase of the stimulus is started.

Next, the control device 100A controls a change amount of a stimulus based on a change of a sleep state with the stimulus (Step S1007). The processing will be described later.

Next, the control device 100A determines whether or not the wake-up set time has arrived, or a sleeper is awakening or has woken up (Step S1008). Specifically, the stimulation control unit 103 determines whether or not the wake-up set time has arrived, and whether or not the sleep stage determined by the determination unit 102 is awakening or wake-up. The determination unit 102 determines whether the sleep stage is awakening or wake-up based on the acquired sleep state. The determination unit 102 may determine whether the sleep stage is awakening or wake-up based on the operation of the operation unit 105. For example, when the operation unit 105 accepts operation of stopping the alarm, determination is made that the sleep stage is awakening or wake-up.

In a case of Yes in Step S1008, i.e., in a case where determination is made that the wake-up set time has arrived, or a sleeper is awakening or has woken up, the control device 100A causes the stimulation device 300 to stop increasing a stimulus (Step S1009). Specifically, in a case where the wake-up set time has arrived or the determined sleep stage is awakening or wake-up, the stimulation control unit 103 causes the stimulation device 300 to stop increasing a stimulus.

In a case of No in Step S1008, i.e., in a case where determination is made that the wake-up set time has not arrived and the sleeper is not awakening or has not woken up, the processing returns to Step S1007. Specifically, in a case where the wake-up set time has not arrived and the determined sleep stage is not awakening or wake-up, the processing returns to Step S1007. The stimulation control unit 103 may stop stimulation depending on a kind of stimulus. For example, in a case where a stimulus is sound or tactile vibration, the stimulation control unit 103 causes the stimulation device 300 to stop stimulation.

Further, using FIG. 8, the processing of Step S1007 will be described. FIG. 8 is a flow chart showing details of a part (i.e., Step S1007) of the processing in the stimulation control system according to the first embodiment of the present disclosure.

First, the control device 100A acquires an interval for altering a change amount of a stimulus (Step S1101). Specifically, the determination unit 102 acquires, from the storage unit 106, a time interval at which a sleep state is acquired as an interval for altering the change amount of a stimulus. A time interval at which a sleep state is acquired is a time interval required for estimating a sleep state. An interval for altering the change amount of a stimulus can be an interval having any arbitrary length that is longer than a time interval required for estimating the sleep.

Next, with respect to each altering interval, the control device 100A determines a change of a body movement amount or of a sleep stage between an immediately preceding section (in other words, a first section) and one mom preceding section (in other words, a second section)(Step S1102). Specifically, the determination unit 102 compares a body movement amount in the first section and a body movement amount in the second section to calculate a change amount of a body movement amount. Additionally, the determination unit 102 calculates a transition of the sleep stage from the second section to the first section.

Next, the control device 100A determines whether or not the change amount of the body movement amount with a stimulus exceeds a defined range or not, or the transition of the sleep stage is faster than a defined transition (Step S1103). Specifically, the stimulation control unit 103 determines whether or not a change of a body movement amount exceeds the defined range. For example, the defined range is a range obtained by adding or subtracting a predetermined value to or from a defined value. The stimulation control unit 103 also determines whether or not the sleep stage makes a transition to a light sleep stage faster than the defined transition. For example, in a case where the defined transition is a transition from a stage 3 to a stage 2, the stimulation control unit 103 determines whether or not the stage 3 makes a transition to a stage 1.

In a case of Yes in Step S1103, i.e., in a case where determination is made that the change amount of the body movement amount with a stimulus exceeds the defined range, or the transition of the sleep stage is faster than the defined transition, the control device 100A causes a stimulus change amount to become less than a defined value (Step S1104). Specifically, in a case where the change of the body movement amount exceeds the defined range, the stimulation control unit 103 causes the change amount of a stimulus to become less than the defined value in accordance with an excess of change. In a case where the sleep stage makes a transition to the light sleep stage faster than the defined transition, the stimulation control unit 103 also causes the change amount of a stimulus to become less than the defined value in accordance with a degree of stage development.

In a case of No in Step S1103, i.e., in a case where determination is made that the change amount of the body movement amount with a stimulus does not exceed the defined range, and the transition of the sleep stage is not faster than the defined transition, the control device 100A determines whether or not the change amount of the body movement amount with a stimulus is less than the defined range, or the transition of the sleep stage is slower than the defined transition or not (Step S1105). Specifically, the stimulation control unit 103 determines whether or not the change of the body movement amount is less than the defined range (e.g., a range obtained by adding or subtracting a predetermined value to or from a defined value). The stimulation control unit 103 also determines whether or not the transition of the sleep stage is slower than the defined transition. For example, in a case where the defined transition is a transition from a stage 3 to a stage 2, the stimulation control unit 103 determines whether or not the stage 3 stagnates.

In a case of Yes in Step S1105, i.e., in a case where determination is made that the change amount of the body movement amount with a stimulus is less than the defined range, or the transition of the sleep stage is slower than the defined transition, the control device 100A causes the stimulus change amount to become larger than the defined value (Step S1106). Specifically, in a case where the change of the body movement amount is below the defined range, the stimulation control unit 103 causes the change amount of a stimulus to become larger than the defined value in accordance with a shortage. Additionally, in a case where the transition of the sleep stage is slower than the defined transition, the stimulation control unit 103 causes the change amount of a stimulus to become larger than the defined value in accordance with a degree of stage stagnation.

In a case of No in Step S1105, i.e., in a case where determination is made that the change amount of the body movement amount with a stimulus is not less than the defined range and the transition of the sleep stage is not slower than the defined transition, the control device 100A causes the stimulus change amount to remain being the defined value (Step S1107). Specifically, the stimulation control unit 103 determines the defined value as a subsequent change amount of a stimulus.

Next, using FIG. 9, a change of a stimulus will be described. FIG. 9 is a graph showing an example of a change of a stimulus amount according to the first embodiment of the present disclosure.

First, when current time reaches a control start time T0, the control device 100A updates the control start time based on an adjustment value specified by a sleep state. For example, the control start time is updated from T0 to D2 (T0'). A change pattern of a stimulus can be shifted in time from a pattern X1 to a pattern X2. Further, the change pattern of the stimulus can be connected at the time of a shift based on a wake-up set time or the like.

When the current time reaches the control start time T0' after the update, the control device 100A starts increasing a stimulus. Increasing a stimulus will be continued at least until the increase reaches a target stimulus amount or until the time reaches the wake-up set time.

In each of intervals D1' to D4' for altering a change amount of a stimulus, the control device 100A controls an altering amount of a stimulus based on a change of asleep state. For example, in an example of a pattern X2a in FIG. 9, an altering amount of a stimulus is increased to be larger than a defined amount, and as compared with the pattern X2 in which a change amount of a stimulus is controlled to be the defined amount, the stimulus amount is more sharply increased. This is control conducted in a case where a change of a sleep state is smaller than defined (e.g., in a case where a transition of a sleep stage is slow). In an example of a pattern X2b in FIG. 9, an altering amount of a stimulus is reduced to be smaller than the defined amount, and as compared with the pattern X2, the stimulus amount is more gradually increased until a wake-up set time T1. This is control conducted in a case where a change of a sleep state is larger than defined (e.g., in a case where a sleep stage quickly makes a transition to alight stage). In a case where the stimulus amount does not reach the target stimulus amount before the wake-up set time T1, the stimulation control unit 103 can continuously increase the stimulus amount until the stimulus amount reaches the target stimulus amount. The stimulation control unit 103 can also increase the stimulus amount until the stimulus amount reaches the target stimulus amount after a lapse of a time Tw after sleeper's awakening or wake-up. Then, an increase of a stimulus is stopped at a time Tn when the stimulus amount reaches the target stimulus amount.

As described in the foregoing, the first embodiment of the present disclosure includes: acquiring time information including a wake-up set time; acquiring a sleep state of a sleeper who is stimulated by a stimulation device; determining a change of the sleep state; causing the stimulation device to start increasing a stimulus which urges the sleeper to awake at a control start time as time before the wake-up set time by a predetermined time period; and controlling a change amount of the stimulus based on the change of the sleep state with the stimulus.

This enables an excess or a deficiency of an awakening level to be suppressed even when sensitivity to the stimulus is different among individuals. Therefore, a difference in an awakening level promoted by a stimulus among individuals can be suppressed. Accordingly, it will be possible to provide comfortable waking and improve a level of satisfaction with sleep.

<1-3. First Modification>

Figure 10:
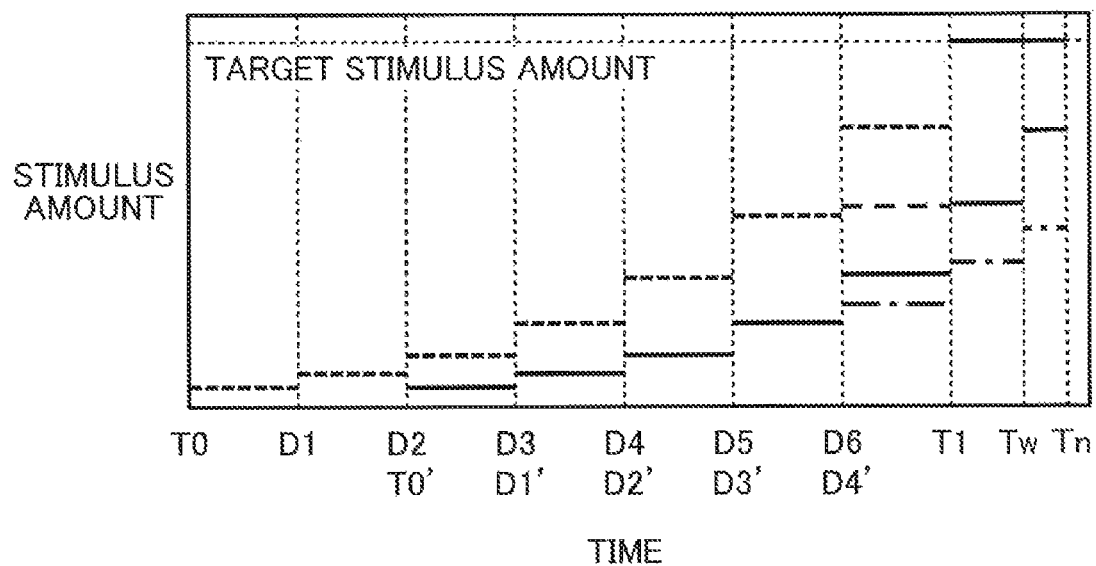
FIG. 10 is a graph showing an example of a change of a stimulus amount according to a first modification of the present disclosure.

A first modification of the first embodiment of the present disclosure will be described. While in the first embodiment, a change amount of a stimulus corresponds to an inclination of an increase of a stimulus (in other words, an increase amount per hour), in the first modification, a change amount of a stimulus corresponds to an increase amount of a stimulus. FIG. 10 is a graph showing an example of a change of a stimulus amount according to the first modification of the present disclosure.

The control device 100A controls a stimulus amount at an interval for altering a change amount of a stimulus. Specifically, the stimulation control unit 103 alters a stimulus amount based on a determined change amount of a stimulus at timing of the interval for altering a change amount of a stimulus. For example, the stimulation control unit 103 maintains a stimulus amount without changing in a section between timings for altering a change amount of a stimulus as shown in FIG. 10. Then, the stimulation control unit 103 determines an increase amount of a stimulus based on a change of a sleep state at the timing for altering a change amount of a stimulus, and causes an increase of a stimulus amount by the determined increase amount. Therefore, a stimulus amount changes in a stepped manner as shown in FIG. 10.

From the foregoing, since no stimulus will change in the above section, i.e., a sleep state measurement period, a change of a sleep state with a stimulus between the above sections adjacent to each other can be more accurately determined as compared with a case where a stimulus changes over time in the above section as in the first embodiment.

<1-4. Second Modification>

Figure 11:
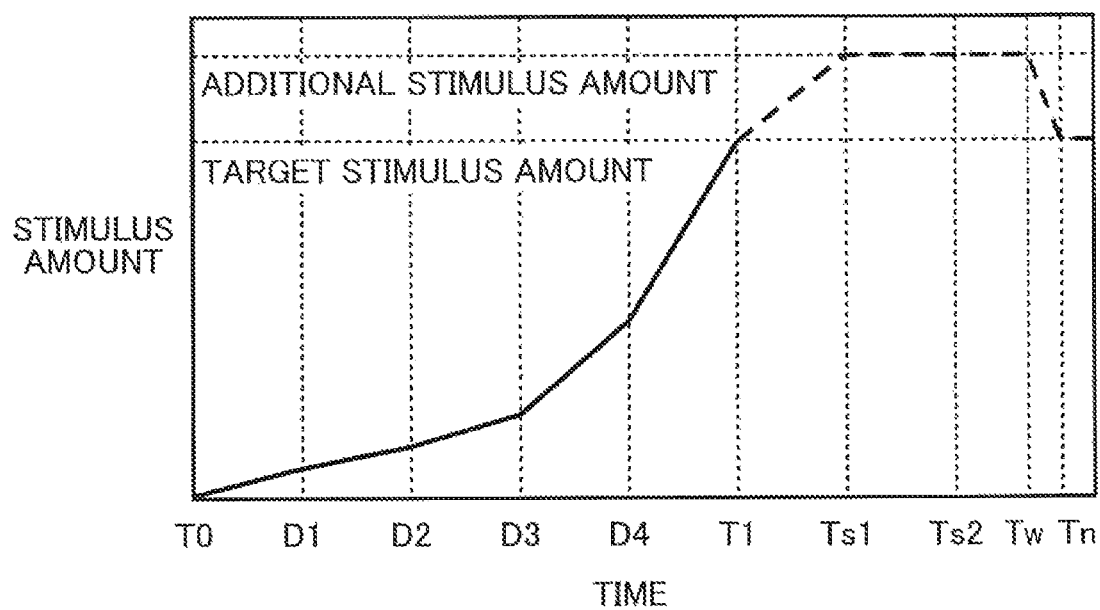
FIG. 11 is a graph showing an example of a change of a stimulus amount according to a second modification of the present disclosure.
Figure 12:
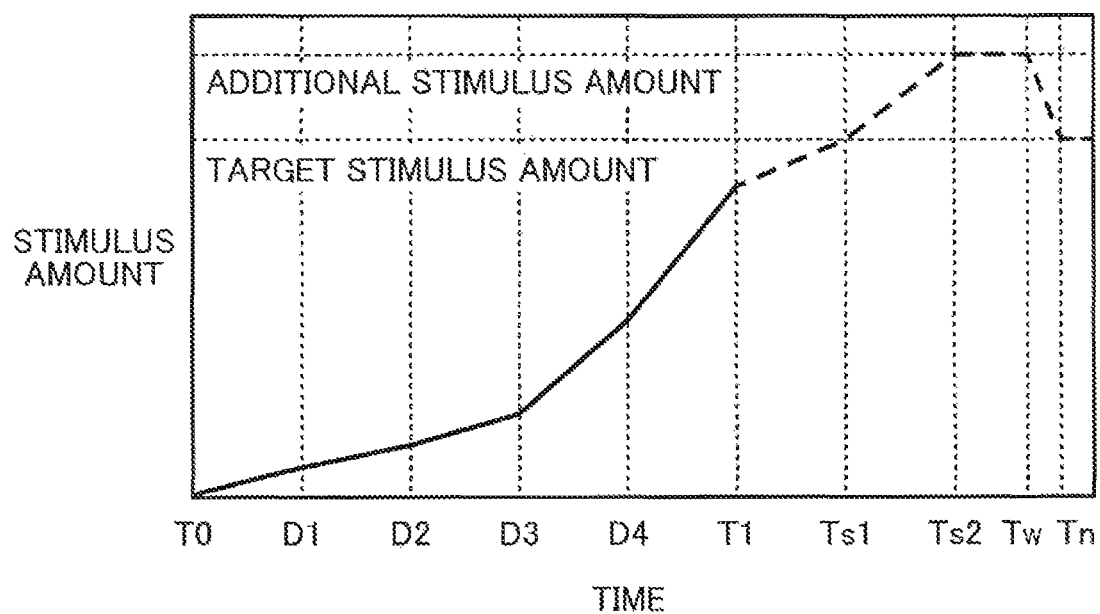
FIG. 12 is a graph showing another example of a change of a stimulus amount according to the second modification of the present disclosure.
Figure 13:
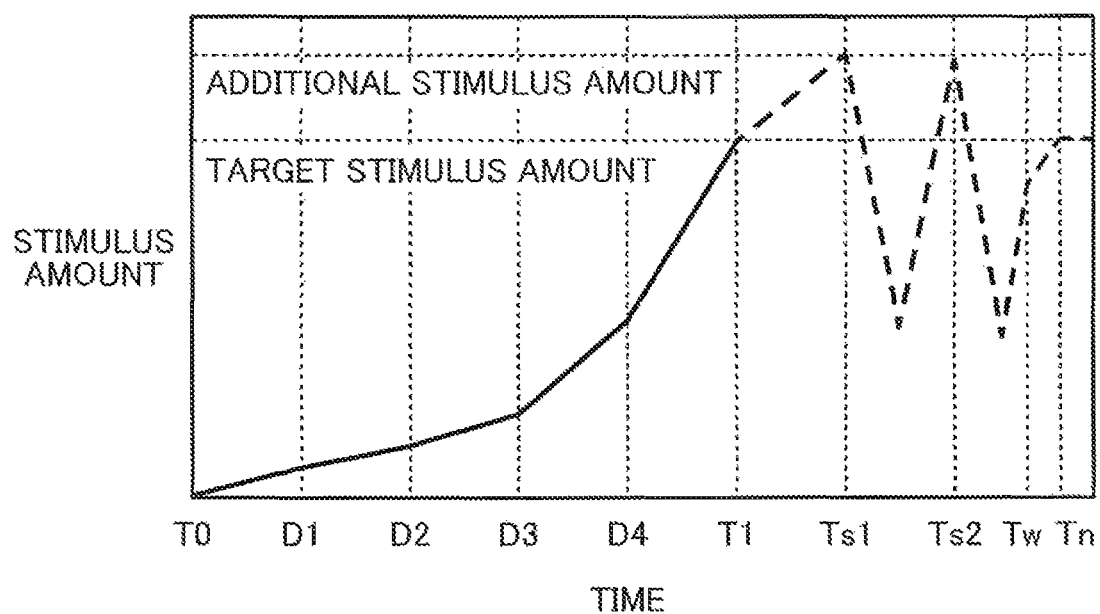
FIG. 13 is a graph showing yet another example of a change of a stimulus amount according to the second modification of the present disclosure.

A second modification of the first embodiment of the present disclosure will be described. While in the first embodiment, increasing a stimulus amount is stopped when the stimulus amount reaches a target stimulus amount, in the second modification, increasing a stimulus amount is continued even after the stimulus amount reaches a target stimulus amount. FIG. 11 to FIG. 13 are graphs showing examples of a change of a stimulus amount in the second modification of the present disclosure.

In a case where a sleeper does not awake even at a wake-up set time, the control device 100A causes a stimulus amount to be increased until it reaches an additional stimulus amount larger than a target stimulus amount. For example, although a stimulus amount reaches the target stimulus amount at the wake-up set time T1 as shown in FIG. 11, in a case where the sleeper is not awakening, the stimulation control unit 103 causes the stimulus amount to be increased until it reaches the additional stimulus amount. Additionally, an increase of a stimulus amount can be controlled such that the stimulus amount reaches the additional stimulus amount at timing Ts1 when the alarm is restarted. In a case where the sleeper does not awake even when the stimulus amount reaches the additional stimulus amount, the stimulus amount can be maintained at the additional stimulus amount until the time Tw when the sleeper awakes as shown in FIG. 11. When the sleeper awakes, the stimulus amount is reduced to the target stimulus amount.

Additionally, in a case where the stimulus amount does not reach the target stimulus amount at the wake-up set time, the control device 100A can control a change amount of a stimulus such that the stimulus amount reaches the target stimulus amount at predetermined timing after the wake-up set time. For example, in a case where the stimulus amount does not reach the target stimulus amount at the wake-up set time T1, the stimulation control unit 103 can control the stimulus amount such that the stimulus amount reaches the target stimulus amount at the timing Ts1, the first timing when the alarm given at the wake-up set time is restarted as shown in FIG. 12. Further, the stimulus amount can be controlled such that the stimulus amount reaches the additional stimulus amount at timing Ts2, the second timing when the alarm is restarted.

The control device 100A can also alter a mode of a change of a stimulus after a lapse of the wake-up set time. For example, the stimulation control unit 103 causes the stimulus amount to be increased until it reaches the additional stimulus amount after a lapse of the wake-up set time T1 as shown in FIG. 13. Thereafter, the stimulation control unit 103 periodically increases or decreases the stimulus amount within a predetermined range as shown in FIG. 13. For example, the stimulation control unit 103 causes the stimulus amount to be increased such that the stimulus amount reaches the additional stimulus amount at the timing Ts1, the first timing when the alarm is restarted after a lapse of the wake-up set time T1. Then, after decreasing the stimulus amount to be smaller than the target stimulus amount in a range from the timing Ts1, the first timing when the alarm is restarted, to the timing Ts2, the second timing when the alarm is restarted, the stimulation control unit 103 again causes the stimulus amount to be increased to the additional stimulus amount Increasing or decreasing the stimulus amount is conducted until a sleeper awakes. After the sleeper awakes, the stimulus amount will be altered to the target stimulus amount. This enables awakening to be more strongly urged than by continuously applying a fixed stimulus.

<1-5. Third Modification>

Figure 14:
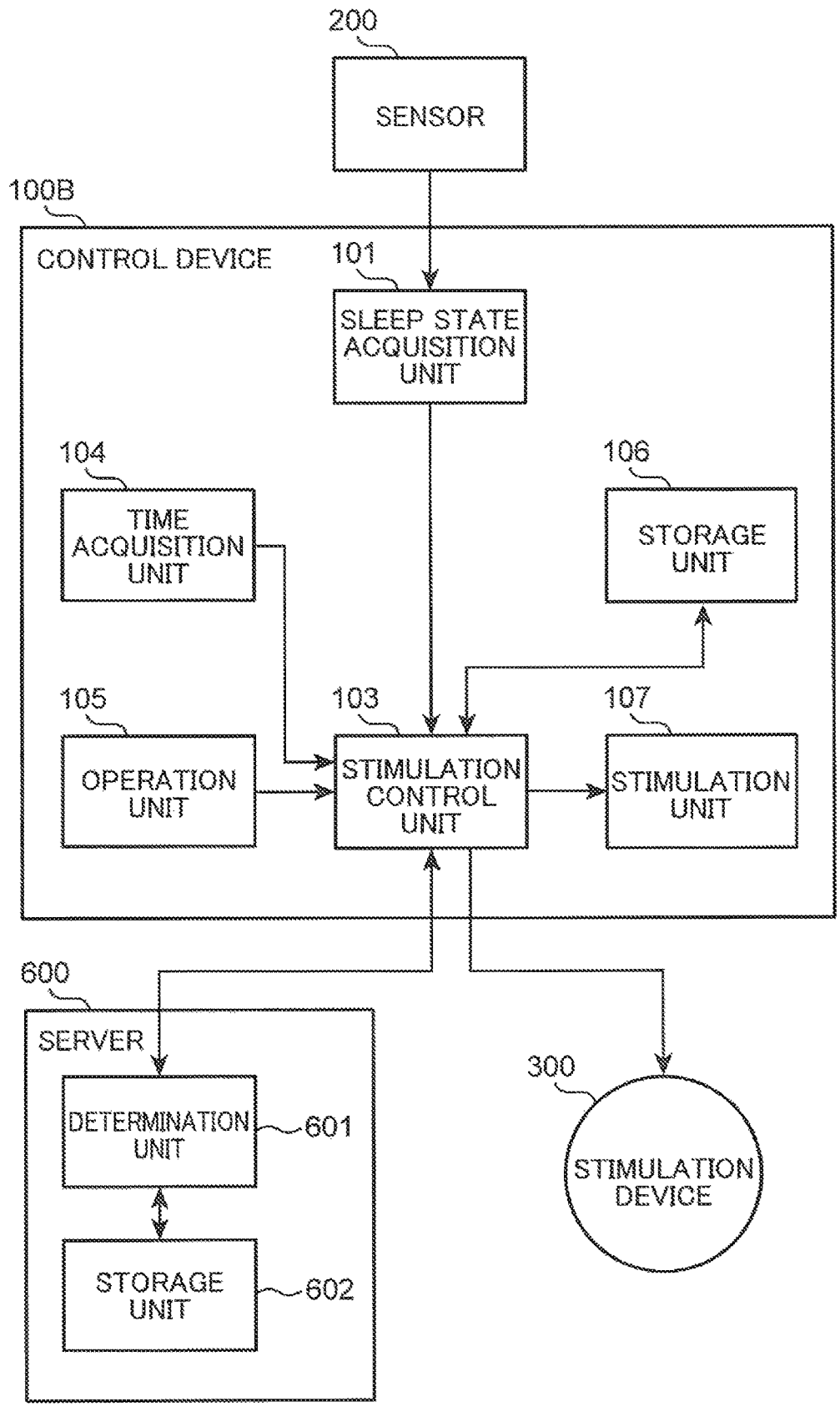
FIG. 14 is a block diagram showing a configuration example of a stimulation control system according to a third modification of the present disclosure.

A third modification of the first embodiment of the present disclosure will be described. While in the first embodiment, the control device 100A determines a change of a sleep state, a server 600 determines a sleep state in the third modification. FIG. 14 is a block diagram showing a configuration example of a stimulation control system according to the third modification of the present disclosure.

The stimulation control system according to the third modification includes the server 600 in addition to a control device 100B, a sensor 200, and a stimulation device 300.

The control device 100B has basically the same configuration as that of the control device 100A except that the determination unit 102 is not provided.

The server 600 includes a determination unit 601 and a storage unit 602. The determination unit 601 has the same function as that of the determination unit 102. Additionally, there is stored, in the storage unit 602, information for determining a change of a sleep state, information being, for example, a sleep state acquired by the sleep state acquisition unit 101. Information, such as a sleep state, is acquired from the control device 100B through communication and stored in the storage unit 602. For example, the storage unit 602 has a capacity larger than a capacity of the storage unit 106. Additionally, the server 600 has processing performance higher than that of the control device 100B.

Thus, a change of a sleep state is determined by the server 600 which has higher calculation resources such as a storage capacity or higher calculation performance such as processing performance than the control device 100B. As mom information is provided for use in determining a sleep state, determination of a change of a sleep state can be made more accurately. It is therefore possible to control a change amount of a stimulus more accurately and to improve a level of satisfaction with sleep. In this case, training of a machine learning model is possible for determining a change of a sleep state.

<1-6. Fourth Modification>

A fourth modification of the first embodiment of the present disclosure will be described. While in the first embodiment, a kind of stimulus is fixed, the kind of stimulus may be altered in the fourth modification.

The control device 100A selects a kind of stimulus in accordance with a change of a sleep state. For example, in a case where a change of a sleep state is smaller than defined, the stimulation control unit 103 selects a stimulus of a strong kind. The stimulation control unit 103 causes a stimulation device which outputs a selected stimulus to output a stimulus and causes the stimulation device before the selection to stop stimulation. The stimulation control unit 103 can combine a plurality of stimuli such that a total amount of the stimuli becomes a defined stimulus amount.

A mode of a stimulus can be altered. The control device 100A selects a mode of a stimulus in accordance with a change of a sleep state. For example, in a case where a change of a sleep state is smaller than defined, the stimulation control unit 103 selects a mode of a strong stimulus. For example, the stimulation control unit 103 selects a mode in which a stimulus amount periodically changes as described in the second modification.

The control device 100A can also select a kind or a mode of a stimulus in accordance with a surrounding environment of a sleeper. For example, in an environment where an illuminance is high such as shining of morning sun, the stimulation control unit 103 selects not light but sound as a kind of stimulus and controls a stimulus by using a speaker.

2. Second Embodiment

Next, a second embodiment of the present disclosure will be described. In the second embodiment, a control start time is adjusted based on quality of sleep.

<2-1. Configuration of Stimulation Control System>

Although a control device 100 according to the second embodiment has the same configuration as that of the control device 100A or 100B according to the first embodiment, the determination unit 102 or the determination unit 601, and the stimulation control unit 103 each have a part of operation thereof different from that of the first embodiment.

The determination unit 102 determines a sleep score by using a sleep state. Specifically, the determination unit 102 determines a sleep score based on a body movement amount, the number of heartbeats, a respiration rate, or the like which have been acquired at the control start time. The sleep score can be determined based on a sleep state in a period from a bedtime start to a control start time.

The stimulation control unit 103 adjusts a control start time based on a sleep score. Specifically, the stimulation control unit 103 causes control start to wait based on a sleep score determined by the determination unit 102. The stimulation control unit 103 can also set an adjustment value of the control start time based on a sleep score based on a change of a sleep state after stimulation starts. For example, in a case where a change of a sleep state is larger than defined, the stimulation control unit 103 causes an adjustment value to be stored in association with a sleep score.

<2-2. Processing of Stimulation Control System>

Subsequently, using FIG. 15, processing of a stimulation control system according to the second embodiment will be described. The second embodiment is different from the first embodiment in the processing added between Step S1002 and Step S1005 shown in FIG. 7. FIG. 15 is a flow chart showing a part of processing of the stimulation control system according to the second embodiment of the present disclosure.

In a case of Yes in Step S1002 shown in FIG. 7, the control device 100 determines a sleep score and a sleep stage by using a sleep state (Step S1201). Specifically, the determination unit 102 determines a sleep score based on a sleep state such as a body movement amount. The determination unit 102 also determines a sleep stage similarly to the first embodiment.

Next, the control device 100 determines whether or not the sleep score is higher than a reference value, or the sleep stage is a stage of sleep deeper than a reference stage (Step S1202). Specifically, the stimulation control unit 103 determines whether or not the sleep score is higher than the reference value set in advance. The stimulation control unit 103 also determines whether or not the sleep stage is a stage of sleep deeper than the reference stage set in advance. The reference value or the reference stage is stored in the storage unit 106.

In a case of No in Step S1202, i.e., in a case where determination is made that the sleep score is not higher than the reference value and that the sleep stage is not a stage of sleep deeper than the reference stage, the control device 100 determines whether or not a remaining time from the current time to a wake-up set time is a predetermined time period or more (Step S1203). Specifically, in a case where sleep quality is lower than reference quality, the stimulation control unit 103 determines whether or not the remaining time from the current time to the wake-up set time is the predetermined time period or more. For example, the predetermined time period as the remaining time is five minutes or the like.

In a case of Yes in Step S1203, the control device 100 waits for the predetermined time period (Step S1204). After waiting, the processing returns to Step S1201. Specifically, in a case where the remaining time from the current time to the wake-up set time is the predetermined time period or more, the stimulation control unit 103 delays a stimulation start time by waiting for the predetermined time period. For example, waiting time is one minute or the like.

In a case of Yes in Step S1202, i.e., in a case where determination is made that the sleep score is higher than the reference value, or that the sleep stage is a stage of sleep deeper than the reference stage, and in a case of No in Step S1203, the processing proceeds to Step S1005 where the stimulation control is started.

Thus, according to the second embodiment of the present disclosure, a control start time is adjusted based on sleep quality. This causes stimulation control for wake-up in a state of high sleep quality to be started. It is therefore possible to provide comfortable waking and improve a level of satisfaction with sleep.

INDUSTRIAL APPLICABILITY

Since the control method, the control device, and the non-transitory computer-readable recording medium recording the program according to the present disclosure enable a difference in an awakening level promoted by a stimulus among individuals to be suppressed, the control method, the control device, and the non-transitory computer-readable recording medium recording the program are useful as a control method, a control device, and a non-transitory computer-readable recording medium recording a program which control a stimulation device that outputs a stimulus.

The invention claimed is:

1. A control method executed by a computer for controlling a stimulation device that outputs a stimulus, the control method comprising:
    acquiring time information including a wake-up set time;
    first acquiring a sleep state of a sleeper who is stimulated by the stimulation device;
    determining a change of the sleep state;
    causing the stimulation device to start increasing the stimulus which urges the sleeper to awake;
    controlling an increase amount of the stimulus based on the change of the sleep state with the stimulus;
    determining whether a control start time preceding the wake-up set time by a first predetermined time period has arrived;
    when the control start time is determined to have arrived, determining whether the control start time has been updated;
    when the control start time is determined not to have been updated, second acquiring the sleep state of the sleeper and updating the control start time using an adjustment value and the second acquired sleep state; and
    causing the stimulation device to start increasing the stimulus at the updated control start time.

2. The control method according to claim 1, wherein
    the sleep state includes a body movement amount of the sleeper, and
    the increase amount of the stimulus is determined based on a defined value in accordance with a relationship between a change of the body movement amount with the stimulus and a defined range.

3. The control method according to claim 2, wherein the increase amount of the stimulus is set to be smaller than the defined value in a case where the change of the body movement amount with the stimulus is larger than the defined range.

4. The control method according to claim 2, wherein the increase amount of the stimulus is set to be larger than the defined value in a case where the change of the body movement amount with the stimulus is smaller than the defined range.

5. The control method according to claim 1, wherein
    the sleep state includes a sleep stage of the sleeper, and
    the increase amount of the stimulus is determined based on the defined value in accordance with a relationship between a transition of the sleep stage in response to the stimulus and a defined transition.

6. The control method according to claim 1, further comprising:
acquiring a change pattern of the stimulus,
controlling the increase amount of the stimulus based on the change pattern of the stimulus; and
using a change of the sleep state with the stimulus to set a change pattern of the stimulus.

7. The control method according to claim 1, wherein the control start time is set using a change of the sleep state with the stimulus.

8. The control method according to claim 1, wherein the increase amount of the stimulus is controlled at an interval of time required for estimating the sleep state.

9. The control method according to claim 1, wherein, in a case where as a result of controlling the increase amount of the stimulus based on a change of the sleep state with the stimulus, an amount of the stimulus fails to reach a target amount at the wake-up set time, the increase amount of the stimulus is controlled so that the amount of the stimulus reaches the target amount at a time following the wake-up set time by a second predetermined time period.

10. The control method according to claim 9, wherein the time following the wake-up set time by the second predetermined time period is time when an alarm to be given at the wake-up set time is restarted after the second predetermined time period.

11. The control method according to claim 1, wherein in a case where, as a result of controlling the increase amount of the stimulus based on a change of the sleep state with the stimulus, an amount of the stimulus fails to reach a target amount at the wake-up set time, the increase amount of the stimulus is controlled so that the amount of the stimulus reaches the target amount after awaking of the sleeper.

12. The control method according to claim 1, wherein a kind of the stimulus or a mode of the stimulus is selected in accordance with a change of the sleep state with the stimulus, and
the increase amount of the stimulus of the selected kind or mode is controlled based on a change of the sleep state with the stimulus of the selected kind or mode.

13. The control method according to claim 1, wherein the stimulus is at least one of light, sound, tactile vibration, wind, and heat.

14. A control device comprising:
a time acquisition unit which acquires time information including a wake-up set time;
a sleep state acquisition unit which first acquires a sleep state of a sleeper who is stimulated by a stimulation device;
a determination unit which determines a change of the sleep state; and
a stimulation control unit which causes the stimulation device to start increasing a stimulus which urges the sleeper to awake, and controls an increase amount of the stimulus based on the change of the sleep state with the stimulus, wherein
the stimulation control unit determines whether a control start time preceding the wake-up set time by a first predetermined time period has arrived,
when the control start time is determined to have arrived, the stimulation control unit determines whether the control start time has been updated,
when the control start time is determined not to have been updated, the sleep state acquisition unit second acquires the sleep state of the sleeper, and the stimulation control unit updates the control start time using an adjustment value and the second acquired sleep state, and
the stimulation control unit causes the stimulation device to start increasing the stimulus at the updated control start time.

15. A non-transitory computer-readable recording medium recording a program for causing a computer to execute:
acquiring time information including a wake-up set time;
first acquiring a sleep state of a sleeper who is stimulated by a stimulation device;
determining a change of the sleep state;
causing the stimulation device to start increasing a stimulus which urges the sleeper to awake;
controlling an increase amount of the stimulus based on the change of the sleep state with the stimulus;
determining whether a control start time preceding the wake-up set time by a first predetermined time period has arrived;
when the control start time is determined to have arrived, determining whether the control start time has been updated;
when the control start time is determined not to have been updated, second acquiring the sleep state of the sleeper and updating the control start time using an adjustment value and the second acquired sleep state; and
causing the stimulation device to start increasing the stimulus at the updated control start time.

* * * * *